United States Patent
Jennerjahn et al.

(10) Patent No.: US 9,688,604 B2
(45) Date of Patent: Jun. 27, 2017

(54) PHOSPHINE LIGAND AND PALLADIUM CATALYSTS BASED THEREON FOR THE ALKOXYCARBONYLATION OF ETHYLENICALLY UNSATURATED COMPOUNDS

(71) Applicant: EVONIK DEGUSSA GMBH, Essen (DE)

(72) Inventors: Reiko Jennerjahn, Sanitz (DE); Samet Gülak, Leverkusen (DE); Xiangjie Fang, Shanghai (CN); Kaiwu Dong, Bo Zhou (CN); Helfried Neumann, Rostock (DE); Ralf Jackstell, Cuxhaven Altenwalde (DE); Matthias Beller, Ostseebad Nienhagen (DE); Robert Franke, Marl (DE); Dieter Hess, Marl (DE); Katrin Marie Dyballa, Recklinghausen (DE); Dirk Fridag, Haltern am See (DE); Frank Geilen, Haltern am See (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/213,435

(22) Filed: Jul. 19, 2016

(65) Prior Publication Data
US 2017/0022234 A1 Jan. 26, 2017

(30) Foreign Application Priority Data
Jul. 23, 2015 (DE) .................. 10 2015 213 918

(51) Int. Cl.
| | | |
|---|---|---|
| *C07C 67/38* | (2006.01) | |
| *C07F 17/02* | (2006.01) | |
| *B01J 31/22* | (2006.01) | |
| *C07F 9/58* | (2006.01) | |
| *C07F 9/6506* | (2006.01) | |
| *C07F 15/00* | (2006.01) | |
| *B01J 31/24* | (2006.01) | |
| *C07F 9/572* | (2006.01) | |
| *C07F 9/655* | (2006.01) | |
| *C07F 9/6553* | (2006.01) | |

(52) U.S. Cl.
CPC .......... *C07C 67/38* (2013.01); *B01J 31/2295* (2013.01); *B01J 31/24* (2013.01); *B01J 31/2404* (2013.01); *B01J 31/2409* (2013.01); *C07F 9/5726* (2013.01); *C07F 9/587* (2013.01); *C07F 9/65066* (2013.01); *C07F 9/65515* (2013.01); *C07F 9/655345* (2013.01); *C07F 15/006* (2013.01); *C07F 17/02* (2013.01); *B01J 2231/321* (2013.01); *B01J 2231/49* (2013.01); *B01J 2531/0208* (2013.01); *B01J 2531/824* (2013.01); *B01J 2531/842* (2013.01)

(58) Field of Classification Search
CPC ........ C07F 17/02; C07C 67/38; B01J 31/2409
USPC ......................... 556/14, 20, 22, 28
See application file for complete search history.

(56) References Cited

U.S. PATENT DOCUMENTS 6,433,242 B1  8/2002 Wiese
7,009,080 B2* 3/2006 Ogaki .................. C07C 211/56
564/307

FOREIGN PATENT DOCUMENTS

DE    10 2008 007081 A1   8/2009
EP      0 662 467 A1       7/1995
EP      1 029 839 A1       8/2000

OTHER PUBLICATIONS

Butler et al., Organometallics, vol. 4, No. 6, pp. 972-980 (1985).*
Khokarale, S. G. et al. Zwitterion enhanced performance in palladium-phosphine catalyzed ethylene methoxycarbonylation. Catalysis Communications 44, 2014, pp. 73-75.
Clegg, William, et al. Highly active and selective catalysts for the production of methyl propanoate via the methoxycarbonylation of ethane. Chem. Commun. 1999, pp. 1877-1878.
Harris, Robin K. et al. NMR Nomenclature, Nuclear Spin Properties and Conventions for Chemical Shifts. Pure Appl. Chem., 2001, 73, pp. 1795-1818.
Harris, Robin K. et al. Further Conventions for NMR Shielding and Chemical Shifts. Pure Appl. Chem., 2008, 80, pp. 59-84.
U.S. Appl. No. 15/213,441, Dong, et al., filed Jul. 19, 2016.
U.S. Appl. No. 15/213,444, Dong, et al., filed Jul. 19, 2016.

(Continued)

Primary Examiner — Porfirio Nazario Gonzalez
(74) Attorney, Agent, or Firm — Smith, Gambrell & Russell, LLP

(57) ABSTRACT

The invention relates to a compound of formula (1)

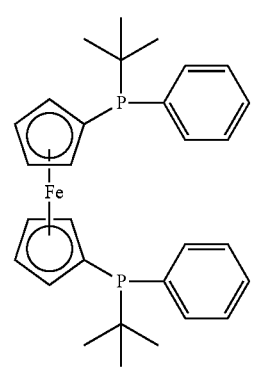

(1)

The invention further relates to Pd complexes comprising the compound according to the invention and to the use thereof in alkoxycarbonylation.

7 Claims, No Drawings

(56) References Cited

OTHER PUBLICATIONS

U.S. Appl. No. 15/213,449, Dong, et al., filed Jul. 19, 2016.
U.S. Appl. No. 15/213,453, Dong, et al., filed Jul. 19, 2016.
U.S. Appl. No. 15/213,456, Dong, et al., filed Jul. 19, 2016.
Search Report and opinion recieved for European Patent Application No. 16180046 dated Jan. 2, 2017 (5 pages).
Bianchini et al. Methoxycarbonylation of Ethene by Palladium(II) Complexes with 1,1'-Bis(diphenylphosphino)ferrocene (dppf) and 1,1'-Bis(diphenylphosphino)octamethylferrecene (dppomf), Organometallics, American Chemical Society, US, 2003, 22, pp. 2409-2421.

* cited by examiner

PHOSPHINE LIGAND AND PALLADIUM CATALYSTS BASED THEREON FOR THE ALKOXYCARBONYLATION OF ETHYLENICALLY UNSATURATED COMPOUNDS

The present invention relates to an improved phosphine ligand and to the use thereof in alkoxycarbonylation.

The alkoxycarbonylation of ethylenically unsaturated compounds is a process of increasing significance. An alkoxycarbonylation is understood to mean the reaction of ethylenically unsaturated compounds such as olefins with carbon monoxide and alcohols in the presence of a metal or a metal complex and a ligand to give the corresponding esters:

Scheme 1: General reaction equation of the alkoxycarbonylation of an ethylenically unsaturated compound

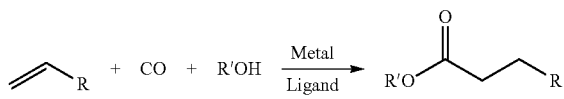

Among the alkoxycarbonylation reactions, ethene methoxycarbonylation to give 3-methylpropionate is of significance as an intermediate stage for the preparation of methyl methacrylate (S. G. Khokarale, E. J. García-Suárez, J. Xiong, U. V. Mentzel, R. Fehrmann, A. Riisager, Catalysis Communications 2014, 44, 73-75). Ethene methoxycarbonylation is conducted in methanol as solvent under mild conditions with a palladium catalyst modified by phosphine ligands.

A very good catalytic system was developed by Lucite—now Mitsubishi Rayon—and uses a ligand based on 1,2-bis (di-tert-butylphosphinomethyl)benzene (DTBPMB) (W. Clegg, G. R. Eastham, M. R. J. Elsegood, R. P. Tooze, X. L. Wang, K. Whiston, Chem. Commun. 1999, 1877-1878).

Applications of methoxycarbonylation to longer-chain substrates are described, for example, in EP 0 662 467 A1. The patent specification describes a process for preparing dimethyl adipate from methyl 3-pentenoate. The Pd source used is Pd(II) acetate. Examples of suitable bidentate phosphine ligands that are cited include 1,1'-bis (diphenylphosphino)ferrocene, 1-(diphenylphosphino)-1'-(diisopropylphosphino)ferrocene and 1,1'-bis (isopropylphenylphosphino)ferrocene. However, the ligands achieve only unsatisfactory yields in the methoxycarbonylation of olefins, especially of long-chain olefins such as 2-octene and di-n-butene.

The technical problem on which the present invention was based is that of providing improved ligands for alkoxycarbonylation reactions. These ligands are to achieve improved yields especially in the conversion of long-chain olefins such as 2-octene or di-n-butene. More particularly, the space-time yield is to be increased in the alkoxycarbonylation reaction.

This object is achieved by a phosphine ligand of formula (1):

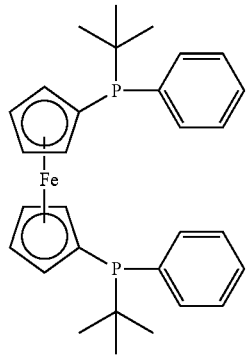

(1)

It has been found that, surprisingly, the phosphine ligand according to the invention, 1,1'-bis-(tert-butylphenylphosphino)ferrocene, has improved properties over the structurally similar ligands described in EP 0 662 467 A1. More particularly, the ligand according to the invention achieves higher yields in the alkoxycarbonylation of long-chain olefins such as 2-octene and di-n-butene.

The invention further relates to complexes comprising Pd and the phosphine ligand according to the invention. In these complexes, the phosphine ligand according to the invention serves as a bidentate ligand for the metal atom. The complexes serve, for example, as catalysts for alkoxycarbonylation. With the complexes according to the invention, it is possible to achieve high yields in the alkoxycarbonylation of a multitude of different ethylenically unsaturated compounds.

The complexes according to the invention may also comprise further ligands which coordinate to the metal atom. These are, for example, ethylenically unsaturated compounds or anions. Suitable additional ligands are, for example, styrene, acetate anions, maleimides (e.g. N-methylmaleimide), 1,4-naphthoquinone, trifluoroacetate anions or chloride anions.

Preferably, the further ligands are selected from N-methylmaleimide, styrene and naphthoquinone.

In one embodiment, the complexes according to the invention are selected from the following complexes K1 to K3:

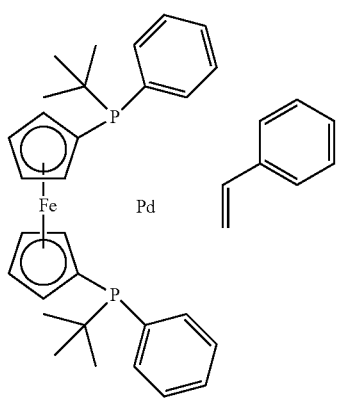

(K1)

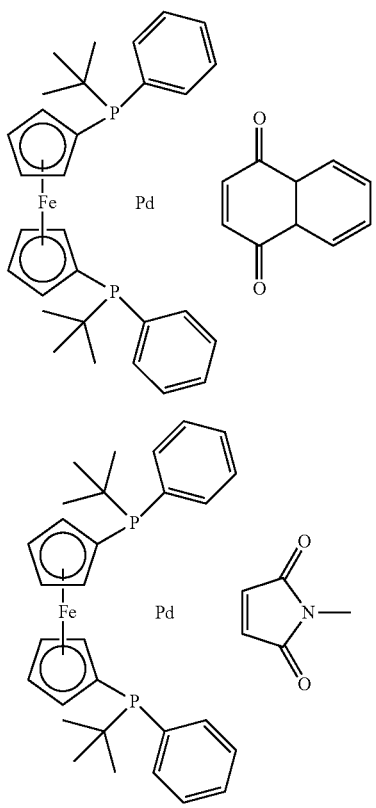

The Pd metal atom may coordinate here to double bonds, double bond systems (such as aromatic or other conjugated systems) or free electron pairs.

The invention further relates to the use of the phosphine ligand according to the invention for catalysis of an alkoxycarbonylation reaction. The phosphine ligand according to the invention can especially be used as a metal complex according to the invention.

The invention also relates to a process comprising the process steps of:
a) initially charging an ethylenically unsaturated compound;
b) adding the phosphine ligand according to the invention and a compound comprising Pd,
  or adding a complex according to the invention comprising Pd and the phosphine ligand according to the invention;
c) adding an alcohol;
d) feeding in CO;
e) heating the reaction mixture, with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound comprises 4 to 30 carbon atoms, preferably 6 to 22 carbon atoms, further preferably 8 to 22 carbon atoms, more preferably 8 to 12 carbon atoms, most preferably 8 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents. At the same time, the ethylenically unsaturated compound preferably comprises a total of 2 to 30 carbon atoms, preferably 2 to 22 carbon atoms, more preferably 2 to 12 carbon atoms.

In one embodiment, the ethylenically unsaturated compound does not comprise any further functional groups apart from carbon-carbon double bonds.

In a particularly preferred embodiment, the ethylenically unsaturated compound is an unfunctionalized alkene having at least one double bond and 2 to 30 carbon atoms, preferably 6 to 22 carbon atoms, further preferably 8 to 22 carbon atoms, especially preferably 8 to 12 carbon atoms, and most preferably 8 carbon atoms.

Suitable ethylenically unsaturated compounds are, for example:
ethene;
propene;
C4 olefins such as 1-butene, cis-2-butene, trans-2-butene, mixture of cis- and trans-2-butene, isobutene, 1,3-butadiene; raffinate I to III, crack-C4
C5 olefins such as 1-pentene, 2-pentene, 2-methyl-1-butene, 2-methyl-2-butene, 2-methyl-1,3-butadiene (isoprene), 1,3-pentadiene;
C6 olefins such as tetramethylethylene, 1,3-hexadiene, 1,3-cyclohexadiene;
C7 olefins such as 1-methylcyclohexene, 2,4-heptadiene, norbornadiene;
C8 olefins such as 1-octene, 2-octene, cyclooctene, di-n-butene, diisobutene, 1,5-cyclooctadiene, 1,7-octadiene;
C9 olefins such as tripropene;
C10 olefins such as dicyclopentadiene;
undecenes;
dodecenes;
internal C14 olefins;
internal C15 to C18 olefins;
linear or branched, cyclic, acyclic or partly cyclic, internal C15 to C30 olefins;
triisobutene, tri-n-butene;
terpenes such as limonene, geraniol, farnesol, pinene, myrcene, carvone, 3-carene;
polyunsaturated compounds having 18 carbon atoms, such as linoleic acid or linoleic acid;
esters of unsaturated carboxylic acids, such as vinyl esters of acetic or propionic acid, alkyl esters of unsaturated carboxylic acids, methyl or ethyl esters of acrylic acid or methacrylic acid, oleic esters, such as methyl or ethyl oleate, esters of linoleic or linolenic acid;
vinyl compounds such as vinyl acetate, vinylcyclohexene, styrene, alpha-methylstyrene, 2-isopropenylnaphthalene;

2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2-pentene, 2-methyl-1-butene, 2-methyl-2-butene, 3-methyl-1-butene, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof.

In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the $C_4$ fraction which arises in naphtha cracking and consists essentially of the isomeric n-butenes, isobutane and n-butane after removal of isobutene from raffinate I. Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which are removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the invention is catalysed by the Pd complex according to the invention. The Pd complex may either be added in process step b) as a preformed complex comprising Pd and the phosphine ligands according to the invention or be formed in situ from a compound comprising Pd and the free phosphine ligand. In this context, the compound comprising Pd is also referred to as catalyst precursor.

In the case that the catalyst is formed in situ, the ligand can be added in excess, such that the unbound ligand is also present in the reaction mixture.

In the case of the complex which is added right at the start as well, it is also possible to add further ligand, such that the unbound ligand is also present in the reaction mixture.

In one variant, the compound comprising Pd is selected from palladium dichloride ($PdCl_2$), palladium(II) acetylacetonate [$Pd(acac)_2$], palladium(II) acetate [$Pd(OAc)_2$], dichloro(1,5-cyclooctadiene)palladium(II) [$Pd(cod)_2Cl_2$], bis(dibenzylideneacetone)palladium [$Pd(dba)_2$], bis(acetonitrile)dichloropalladium(II) [$Pd(CH_3CN)_2Cl_2$], palladium(cinnamyl) dichloride [$Pd(cinnamyl)Cl_2$].

Preferably, the compound comprising Pd is $PdCl_2$, $Pd(acac)_2$ or $Pd(OAc)_2$. $Pd(acac)_2$ is particularly suitable.

The alcohol in process step c) may be branched or linear, cyclic, alicyclic, partly cyclic or aliphatic, and is especially a $C_1$- to $C_{30}$-alkanol. It is possible to use monoalcohols or polyalcohols.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, aryl, heteroaryl or silyl groups and/or halogen substituents.

In one embodiment, the alcohol does not comprise any further functional groups except for hydroxyl groups.

The alcohol may contain unsaturated and aromatic groups. However, it is preferably an aliphatic alcohol.

An aliphatic alcohol in the context of this invention refers to an alcohol which does not comprise any aromatic groups, i.e., for example, an alkanol, alkenol or alkynol.

In one embodiment, the alcohol is an alkanol having one or more hydroxyl groups and 1 to 30 carbon atoms, preferably 1 to 22 carbon atoms, more preferably 1 to 12 carbon atoms, most preferably 1 to 6 carbon atoms.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, phenol, 2-ethylhexanol, isononanol, 2-propylheptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, phenol, or mixtures thereof.

In one variant of the process, the alcohol in process step c) is selected from the group of the polyalcohols.

In one variant of the process, the alcohol in process step c) is selected from: diols, triols, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethylpropane-1,3-diol, 1,2,6-trihydroxyhexane, pentaerythritol, 1,1,1-tri(hydroxymethyl)ethane, catechol, resorcinol and hydroxyhydroquinone.

In one variant of the process, the alcohol in process step c) is selected from: sucrose, fructose, mannose, sorbose, galactose and glucose.

In a preferred variant of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) or methylene chloride ($CH_2Cl_2$).

CO is fed in in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the ethylenically unsaturated compound to an ester.

The molar ratio of the ethylenically unsaturated compound initially charged in step a) to the alcohol added in step c) is preferably between 1:1 and 1:20, more preferably 1:2 to 1:10, especially preferably 1:3 to 1:4.

The mass ratio of Pd to the ethylenically unsaturated compound initially charged in step a) is preferably between 0.001% and 0.5% by weight, more preferably between 0.01% and 0.1% by weight, especially preferably between 0.01% and 0.05% by weight.

The molar ratio of the phosphine ligand according to the invention to Pd is preferably between 0.1:1 and 400:1, more preferably between 0.5:1 and 400:1, especially preferably between 1:1 and 100:1, most preferably between 2:1 and 50:1.

Preferably, the process is conducted with addition of an acid. In one variant, the process therefore additionally comprises step c'): adding an acid to the reaction mixture. This may preferably be a Brønsted or Lewis acid.

Suitable Brønsted acids preferably have an acid strength of $pK_a \leq 5$, more preferably an acid strength of $pK_a \leq 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, nnethanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, nnethanesulphonic acid, trifluoromethanesulphonic acid and p-toluenesulphonic acid.

A Lewis acid used may, for example, be aluminum triflate.

In one embodiment, the amount of acid added in step c') is 0.3 to 40 mol %, preferably 0.4 to 15 mol %, more preferably 0.5 to 5 mol %, most preferably 0.6 to 3 mol %, based on the molar amount of the ethylenically unsaturated compound used in step a).

EXAMPLES

The examples which follow illustrate the invention.
General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}P$ NMR signals were referenced as follows: $SR_{31P} = SR_{1H} * (BF_{31P}/BF_{1H}) = SR_{1H} * 0.4048$ (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of 1,1'-bis(tert-butylphenylphosphino)ferrocene

Scheme 2: Synthesis of 1,1'-bis(tert-butylphenylphosphino)ferrocene

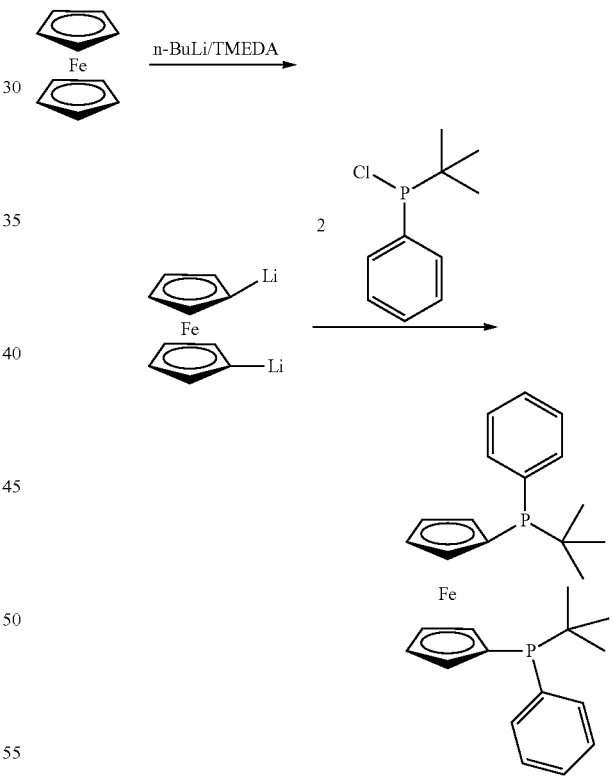

In a 250 ml three-neck flask, 3 g of ferrocene were dissolved under argon in 70 ml of heptane. 5.3 ml of tetramethylethylenediamine (TMEDA) and then 22 ml of 1.6 N butyllithium in hexane were added thereto. The reaction mixture was left to stand at room temperature for 24 hours, then the supernatant solvent was removed. 70 ml of heptane were added to the residue. 6.1 ml of chloro-tert-butylphenylphosphine were dissolved in 20 ml of heptane and this solution was added dropwise to the solution in the three-neck flask. The reaction mixture was heated for 1 hour, then cooled down to room temperature and subjected to aqueous workup. The organic phase was concentrated to dryness. The product was crystallized from hot methanol and filtered. The yield was 4 g.

$^{31}$P NMR (CD$_2$Cl$_2$, 121 MHz), s 8.1 ppm $^1$H NMR (CD$_2$Cl$_2$, 300 MHz), 7.65-7.55 m (4 H), 7.35-7.25 m (6H), 4.2-4.15 m (1 H), 4.2-4.15 m (1H), 4.15-4.0 m (1 H), 4.0-3.95 m (2 H), 3.9-3.85 m (3 H), 0.8 d J=12.4 Hz (18 H), $^{13}$C (CD$_2$Cl$_2$, 75 MHz), 137.7 d, J=14 Hz, 137.4 d, J=12.4 Hz, 136.1 d, J=1.9 Hz, 135.8 d, J=1.5 Hz, 129.3 d, J=4.2 Hz, 127.9 d, J=9 Hz, 77.6 d, J=33.9 Hz, 77.0 d=31.8 Hz, 75.1 d, J=16.8 Hz, 72.9 s, 72.8 s, 72.6 s, 72-71.8 m, 31-30.8 m, 28.2 d, J=14.8 Hz Alternative Synthesis Route to Compound 1

Scheme 3: Synthesis of 1,1'-bis(tert-butylphenylphosphino)ferrocene

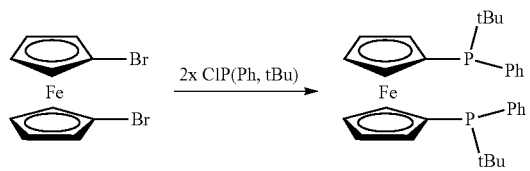

1,1'-Dibromoferrocene (5.22 g, 15.2 mmol) was initially charged in 50 ml of THF. At −60° C., a butyllithium solution (9.5 ml, 15.2 mmol, 1.6 M in hexane) was then added dropwise within about 15 min. The reaction solution was then stirred for about a further 15 min, in the course of which it was warmed slightly (−30° C.). Then the mixture was cooled back down to −60° C., a chloro-tert-butylphenylphosphine solution (3.05 g, 15.2 mmol, in 10 ml of THF) was added within about a further 15 min and then the mixture was warmed to room temperature. This was repeated once more. After the reaction, the solvent was removed and replaced by diethyl ether (50 ml). Then the mixture was washed twice with 25 ml of H$_2$O and dried over MgSO$_4$. Concentration results in precipitation of a rust-coloured precipitate, which was washed with cold diethyl ether. It was possible to obtain 7.28 g (71%) of product. For analysis see previous experiment.

Preparation of 1-(diphenylphosphino)-1'-(diisopropylphosphino)ferrocene (Comparative Compound)

Scheme 4: Synthesis of 1-(diphenylphosphino)-1'-(diisopropylphosphino)-ferrocene

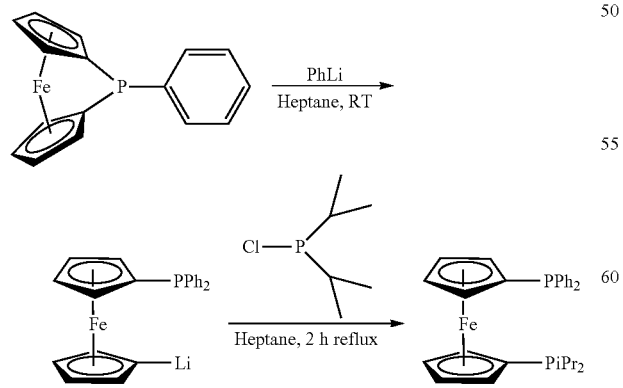

A 50 ml round-bottom flask with magnetic stirrer bar and nitrogen attachment is initially charged with 1.13 mmol (565 µl) of phenyllithium (PhLi), and a solution of 1.03 mmol (300 mg) of cyclic phosphine in 20 ml of heptane is slowly added dropwise via a syringe pump. The Li salt is washed twice with heptane and admixed with 6 ml of heptane. A heptane solution of 0.8 eq (0.824 mmol, 131 µl) of ClPiPr$_2$ in 7 ml of heptane is added dropwise to the suspension at room temperature. The red-brown suspension barely changes colour. After stirring for 20 min, the suspension is heated under reflux for 1.5 hours. The solid turns a somewhat lighter colour. Solvent is removed completely and the brown-red residue is taken up in H$_2$O and ether. The organic phase is washed twice with H$_2$O and dried over Na$_2$SO$_4$. A $^{31}$P spectrum of the ether phase is recorded. The spectrum shows 2 singlets. The chlorophosphine has been fully consumed. The ether phase is dried and 300 mg (yield: 61%) of a brown-yellow oil are obtained, which dissolves in MeOH on a water bath at 65° C. The solution is put in the freezer (−78° C.) overnight. 76 mg of a brown-yellow oil precipitate out, which is analysed by NMR spectroscopy.

$^1$H NMR (300 MHz, CDCl$_3$) δ 7.46-7.23 (m, 10H, Ph), 4.36 (m, 2H, Cp), 4.21 (m, 2H, Cp), 34.24 (m, 4H, Cp), 1.88 (m, 2H, iPr), 1.15-0.96 (m, 12H, iPr).

$^{13}$C NMR (75 MHz, CDCl$_3$) δ 139.9(J=9.8 Hz, Ph), 133.4 (J=19.2 Hz, Ph), 128.4, 128.1, 128.0 (Ph), 77.1, 76.8, 76.2, 76.1 (Cp), 73.5 (J=14.5 Hz, Cp), 72.8 (J=2.9 Hz, Cp), 71.9 (J=10.5 Hz, Cp),72.1 (Cp), 23.3 (J=11.0 Hz, iPr), 20.1, 20.0, 19.9, 19.8 (iPr).

$^{31}$P NMR (121 MHz, C$_6$D$_6$) δ=0.88 and −16.62

Preparation of 1-(diphenylphosphino)-1'-(dicyclohexylphosphino)ferrocene (Comparative Compound)

Scheme 5: Synthesis of 1-(diphenylphosphino)-1'-(dicyclohexylphosphino)ferrocene

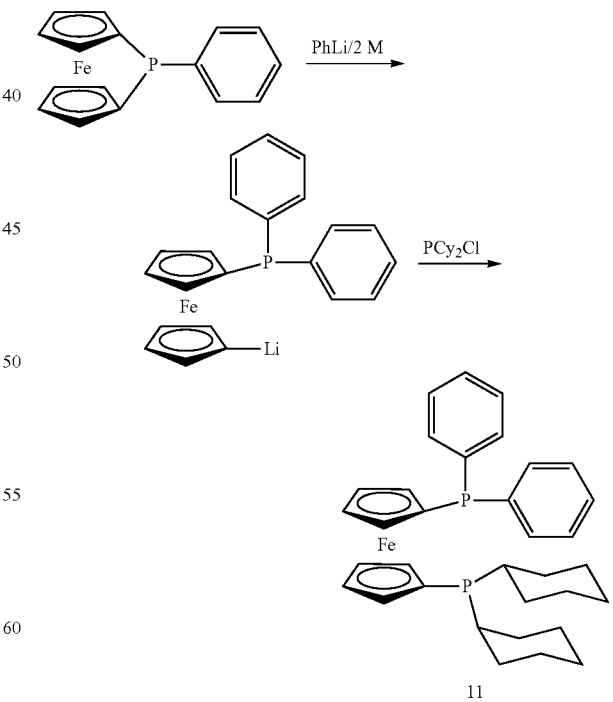

Chemicals used: 0.6 ml of 2 M/THF phenyllithium, 0.25 ml of chlorodicyclohexylphosphine, 50 ml of heptane, 20 ml of THF, 30 ml of diethyl ether, 20 ml of methanol The starting material was dissolved in 30 ml of heptane in a 100 ml Schlenk flask. The phenyllithium was initially charged in a 100 ml three-neck flask. The solution is then slowly added dropwise to the phenyllithium and then left to stand for 1 hour. The reaction solution is then concentrated to about 15 ml. It is then left to stand for 30 min. The supernatant liquid is removed. 20 ml of heptane are added to the residue. The PCy$_2$Cl is dissolved in 20 ml of THF and added within half an hour. The reaction solution is then boiled under reflux for 1 h. The reaction solution is then cooled down to room temperature and a solvent exchange for diethyl ether is undertaken. This is followed by aqueous workup. The Et$_2$O is drawn off. The residue is dissolved in hot methanol. The still-hot solution is filtered. A yellow solid precipitates out in the cold state. The yield is 300 mg.

$^{31}$P(CDCl$_3$, 121 MHz), −7.2 s, −16.8 s $^{13}$C (75 MHz, CDCl$_3$), 133.4 (d, J=19.3 Hz), 128.5 s, 128.2 (d, J=6.8 Hz), 73.6 (d, J=14.4 Hz), 72.9 (d, J=4.9 Hz), 72.3 (d, J=10.5 Hz), 71.2 bs, 69.1 s, 33.5 (d, J=11.5 Hz), 30.4 (d, J=4.9 Hz), 30.2 (d, J=10.2 Hz), 27.4 (dd), 26.4 s $^1$H (300 MHz, CDCl$_3$), 7.3-7.2 m (10 H), 4.2 (t, J=1.7 Hz, 2H), 4.13 t, J=1.7 Hz, 2H), 3.98 (quint, J=1.8 Hz, 4H), 1.8-1.5 (m, 11H), 1.8-1.2 m, 11 H)

Preparation of 1-(diphenylphosphino)-1'-(diadamantylphosphino)ferrocene (Comparative Compound)

Scheme 6: Synthesis of 1-(diphenylphosphino)-1'-(diadamantylphosphino)-ferrocene (Ad: adamantyl)

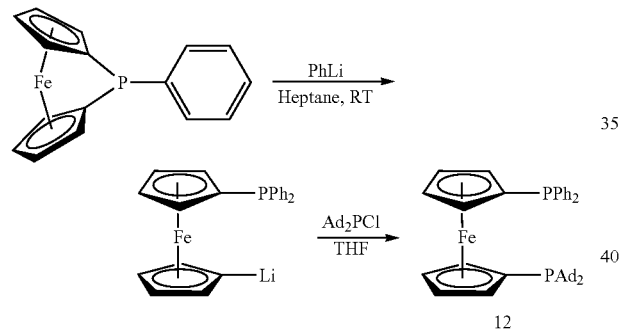

A 100 ml round-bottom flask with magnetic stirrer bar and nitrogen attachment is initially charged with 565 μl (1.13 mmol, 1.1 eq) of PhLi (2M). Within 2 hours, a solution of 300 mg (1.03 mmol) of bridged phosphine and 20 ml of heptane is added dropwise with a syringe pump (0.1 factor 10, 10 ml syringe). After ⅓ of solution has been added, an orange solid precipitates out. After the dropwise addition, the mixture is stirred for a further hour. The dark solution is decanted and washed twice with 6 ml each time of heptane. 6 ml of heptane are added to the orange solid and the chlorophosphine (1.1 eq), dissolved in 7 ml of THF, is added dropwise to the suspension at 0° C. The solution is left to warm up to room temperature while stirring overnight. The suspension has changed colour to become an orange/red clear solution. After addition of 200 μl of water, the solution is dried and the residue is taken up in ether and water. The aqueous phase is highly alkaline (pH paper). After the red organic phase has been washed, it is washed twice with water and dried over Na$_2$SO$_4$. After the ether has been drawn off, what remains is an orange solid.

To complete the reaction, the mixture was heated under reflux for 2 hours. The amount of Ad$_2$PCl was lowered from 1.1 eq to 1.0 eq. According to $^{31}$P NMR, in spite of reflux, there was no further conversion. After integration of the phosphorus signals, 50 mol % of desired product, 28 mol % of Ad$_2$PCl and probably 13 mol % of mono product were obtained. Red crystals have precipitated out of the solution (yield of red crystals 160 mg). These are the desired target product.

$^{31}$P NMR δ=26.0-17.0;

ESI: C$_{42}$H$_{49}$FeP$_2$: calc. 671.26542, found 671.2664

$^1$H NMR (300 MHz, C$_6$D$_6$) δ 7.31-7.13 (m, 10H, Ph), 4.28 (m, 2H, Cp), 4.19 (m, 2H, Cp), 4.01 (m, 2H, Cp), 3.99 (m, 2H, Cp), 1.94-1.61 (m, 18H, Ad), 1.54 (m, 12H, Ad).

$^{31}$P NMR (121 MHz, C$_6$D$_6$) δ=26.04 and −17.00.

Preparation of 1-(diphenylphosphino)-1'-(tert-butylphenylphosphino)ferrocene (Comparative Compound)

Scheme 7: Synthesis of 1-(diphenylphosphino)-1'-(tert-butylphenylphosphino)ferrocene

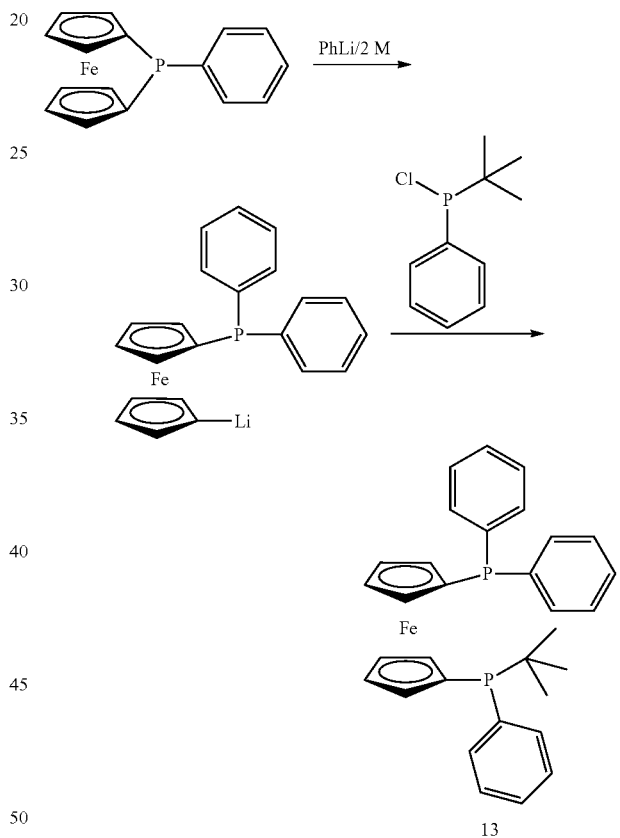

Chemicals Used:

0.53 ml of 2 M/THF phenyllithium, 0.19 ml of tert-butylchloro(phenyl)phosphine, 50 ml of heptane, 20 ml of THF, 30 ml of diethyl ether, 20 ml of methanol The starting material was dissolved in 30 ml of heptane in a 100 ml Schlenk flask. The phenyllithium was initially charged in a 100 ml three-neck flask. The solution was then slowly added dropwise to the phenyllithium at −70° C. and then left to stand for 1 hour. The reaction solution is then concentrated to about 15 ml. It is then left to stand for 30 min. The supernatant liquid is removed. 20 ml of heptane are added to the residue. The tert-butylchloro(phenyl)phosphine is dissolved in 20 ml of THF and added within half an hour. The reaction solution is then boiled under reflux for 1 h. The reaction solution is then cooled down to room temperature and a solvent exchange for diethyl ether is undertaken. This is followed by aqueous workup. The Et$_2$O is drawn off. The residue is dissolved in hot methanol. The still-hot solution is filtered. A yellow solid precipitates out in the cold state.

$^{31}$P (CDCl$_3$ (121 MHz)) 8.1 s, −16.8 s

Preparation of 1,1'-bis(isopropylphenylphosphino)ferrocene (Comparative Compound)

Scheme 8: Synthesis of 1,1'-bis(isopropylphenylphosphino)ferrocene

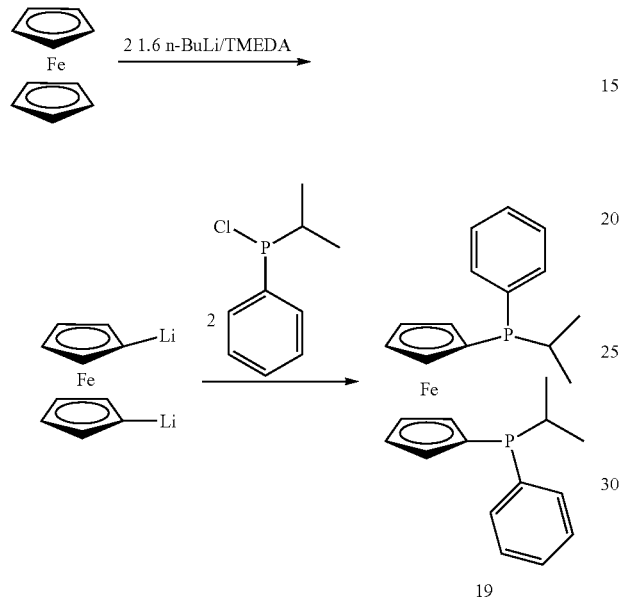

0.93 g of ferrocene is dissolved in 50 ml of absolute heptane in a 100 ml three-neck flask provided with a thermometer, magnetic stirrer and reflux condenser. 1.3 g of TMEDA (1.6 ml) and 7.5 ml of 1.6 M n-BuLi/hexane are added by means of syringes at room temperature. The solution is left to stand for 5 hours. Large orange/brown crystals of the dilithiated ferrocene precipitate out. The supernatant solution is removed by means of a syringe. And 20 ml of absolute heptane are added. Subsequently, the chlorophosphine dissolved in 10 ml of heptane is added dropwise. The mixture is heated under reflux for one hour. After cooling, the organic phase is washed three times with 10 ml each time of degassed water. The mixture is concentrated to dryness, and 10 ml of diethyl ether are added. This solution is filtered through 10 cm of silica gel 60 under argon with diethyl ether as solvent, concentrated to dryness and crystallized from a little hot methanol to give the target product in an about 50% non-optimized yield.

$^{31}$P (121 MHz, CDCl$_3$), −7.8 s, −8.15 s, $^{13}$C (75 MHz, CDCl$_3$); 137.77 (d, J=12 Hz), 137.4 (d, J=11.3 Hz), 134.2 (d, J=20.3 Hz), 129.1 s, 128.1 (d, J=7.5 Hz), 77.4 (d, J=11.3 Hz), 75.0 (d, J=26.2 Hz), 74.0 (d, J=22.3 Hz), 72.1 bs, 71.9-71.5 m, 71.1 s, 69.0 s, 27.6 (d, J=10 Hz), 27.55 (d, J=10 Hz), 20.3-19.9 m $^1$C NMR (300 MHz, CDCl$_3$): 7.52-7.44 (m, 4H), 7.33-7.23 (m, 6H), 4.23 (sept, J=1.2 Hz, 1H), 4.1-4.0 (m, 4 H), 3.93-3.9 (m, 1H), 3.87-3.84 (m, 1H), 3.58-3.54 (m, 1H), 2.1-1.9 (m, 2 H), 0.99 (d, J=7 Hz, 3H), 0.94 (d, J=7 Hz, 3 H), 0.83-0.7 (m, 6H)

Preparation of 1,1'-bis(di(1,4-di(trifluoromethyl)phenyl)phosphino)ferrocene (Comparative Compound)

Scheme 9: Synthesis of 1,1'-bis(di(1,4-di(trifluorormethyl)-phenyl)phosphino)ferrocene

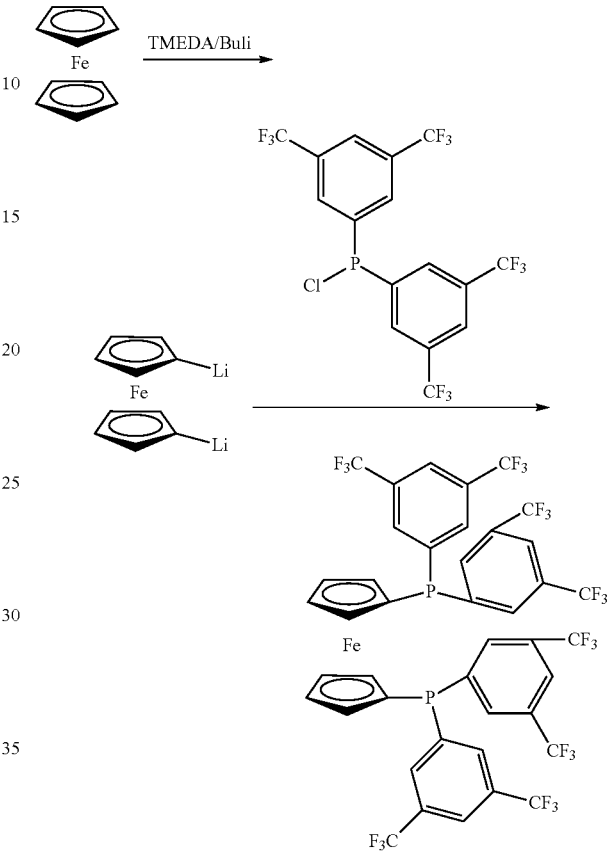

Chemicals used: 0.3 g of ferrocene, 0.61 ml of TMEDA, 2.45 ml of butyllithium, 1.75 ml of PClR$_2$ The ferrocene is dissolved in 15 ml of heptane in a 100 ml three-neck flask. Then TMEDA is added. The butyllithium is likewise added after the addition of TMEDA. The 100 ml flask containing the reaction mixture is left to stand at room temperature for 24 h. After the 24 h, the supernatant solvent is removed. 20 ml of heptane are then added to the residue. First of all, PClR$_2$ is dissolved in 10 ml of heptane. This is then added dropwise to the flask. The reaction is then heated at 70° C. for 30 min, then cooled down to room temperature and subjected to aqueous workup. The organic phase is concentrated to dryness and then crystallized from hot methanol. Yield: 850 mg Analysis:

$^{31}$P (CD$_2$Cl$_2$; 121 MHZ), −14.7 s,

HRMS calculated for 1129.00242, found: 1129.00236

MS EI 70 eV) M/z (%), 1098 (M+, 17) 930 (63), 670(81), 473(100), 319(9.88), 261(16), 195(71), 97(13), 69(23)

Further Comparative Compounds

The comparative compounds 1-(di-tert-butylphosphino)-1'-(diphenylphosphino)ferrocene and 1,2-bis(di-tert-butylphosphinomethyl)benzene used hereinafter are commercially available.

Preparation of [Pd((Cp₂Fe)1,1'-(PPh(t-butyl))₂)(η²-styrene)] (phenyl-η²-ethene) (Complex K1)

Scheme 10: Synthesis of complex K1

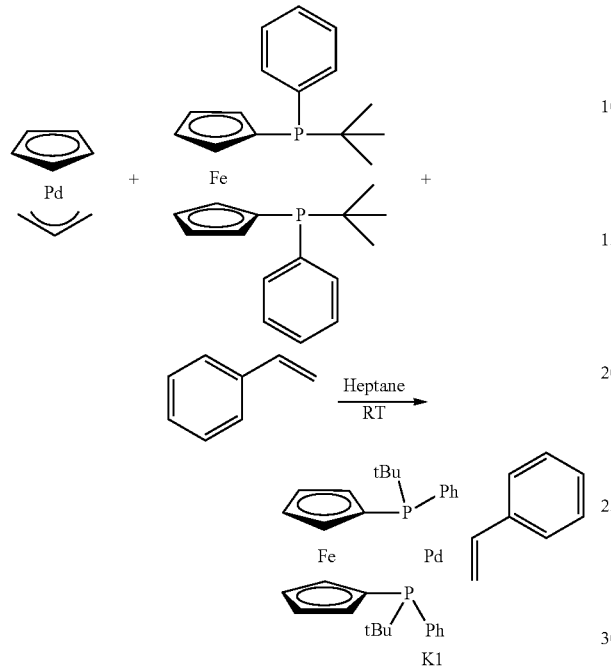

K1

109.6 mg (0.517 mmol) of (η³-allyl)-(η⁵-cyclopentadienyl)palladium is dissolved in about 10 ml of heptane and filtered through Celite. 250.8 mg (0.486 mmol) of ferrocene ligand—dissolved in 10 ml of heptane—together with 55.8 μl (0.486 mmol) of styrene are added dropwise to the clear, deep red solution at room temperature. The colour of the dark red solution lightens after stirring for a few minutes. After one hour, an NMR sample is sealed and a ³¹P NMR is recorded. The ligand has been fully converted. The solution is left to stir for a further four hours and then stored at −28° C. No crystals are formed. The reaction solution is then concentrated to a high degree under high vacuum and a yellow solid precipitates out. To complete the reaction, the suspension is put in the freezer at −28° C. overnight. The supernatant solution is decanted and the yellow solid is washed three times with heptane and dried at the oil pump. Yield: 40-60%. The phosphorus spectrum shows two large signals each split slightly to doublets, and two broader signals.

¹H NMR (300 MHz, C₆D₆) δ 8.53-6.71 (m, 10H, Ph), 5.03-3.27 (m, 8H, Cp), 1.47-1.04 (m, 18H, tBu).

³¹P NMR (121 MHz, C₆D₆) δ=44.91 (d, J=20.3 Hz), 41.27 (d, J=20.3 Hz), 44.01 (br), 39.89 (br).

The phosphorus signals indicate that diastereomeric complexes have formed because of diastereomeric ligands.

Preparation of [Pd((CP₂Fe)1,1'-(PPh(t-butyl))₂)(η²-naphthoquinone)] (Complex K2)

For the complex synthesis, naphthoquinone was used in order to obtain a complex having good crystallizability.

Scheme 11: Synthesis of complex K2

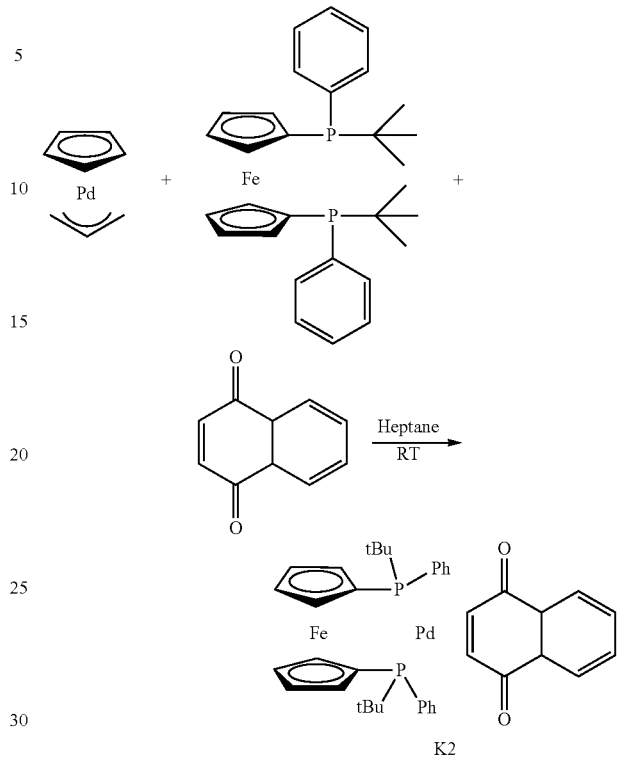

K2

It is important in this reaction is that the naphthoquinone sublimes before the reaction (100° C. and 1·10⁻³ mbar). Sublimed naphthoquinone is a yellow crystalline solid.

109.6 mg (0.516 mmol) of palladium precursor (see Scheme 11) are dissolved in 10 ml of heptane and filtered through Celite into a 25 ml round-bottom flask. 250.8 mg (0.487 mmol) of ferrocene ligand and 76.86 mg (0.485 mmol, 1.1 eq) of freshly sublimed naphthoquinone (dissolved in 15 ml of heptane) are added dropwise to the deep red, clear solution at room temperature. The solution comprising ligand and naphthoquinone is clear and orange in colour. For the complete dissolution of the naphthoquinone, the solution has to be heated to 60° C. with a water bath (and possibly with an ultrasound bath to achieve complete dissolution). The reaction solution lightens in colour and a red/brown solid precipitates out. The mixture is left to stir overnight. After the solids have settled out, the solution is decanted and the red/brown solid is washed twice with heptane. After drying under reduced pressure, a red/brown solid is obtained (50%-70%).

This is an isomer mixture which, in the ³¹P NMR, shows 6 different phosphorus signals and suggests 3 diastereomeric complexes.

¹H NMR (300 MHz, C₆D₆) δ 8.40-8.27 (m, 1.5H, CH arom), 8.17 (m, 0.5H, CH arom), 8.09-87.99 (m, 1H, CH arom), 7.69-7.59 (m, 1H, CH arom), 7.49 (m, 1H, CH arom), 7.30-7.12 (m, 7H, CH arom), 7.08 (m, 1H, CH arom), 6.94-6.66 (m, 3H, CH arom), 5.21-4.98 (m, 2H, CH vinyl), 4.34 (m, 0.5H, Cp), 4.10 (m, 1H, Cp), 4.02 (m, 1H, Cp), 3.95 (m, 0.5H, Cp), 3.90-3.81 (m, 1H, Cp), 3.79 (m, 0.5H, Cp), 3.75 (m, 1H, Cp), 3.66 (m, 0.5H, Cp), 3.60 (m, 1H, Cp), 3.48 (m, 1H, Cp), 1.26-1.06 (m, 18H, tBu).

³¹P NMR (121 MHz, C₆D₆) δ=50.89 (d, Hz, J=25.8 Hz), 47.37 (d, Hz, J=25.8 Hz), 49.58 (s), 46.73 (s).

Elemental analysis calculated for $C_{40}H_{42}FeO_2P_2Pd$: C, 61.67; H, 5.43; P, 7.95. Found: C, 61.36; H, 5.56; P, 7.65.

Preparation of $[Pd((Cp_2Fe)1,1'-(PPh(t-butyl))_2)(\eta^2-N\text{-methylmaleimide})]$ (Complex K3)

It is likewise possible to prepare the palladium complex with N-methylmaleimide as well:

Scheme 12: Synthesis of complex K3

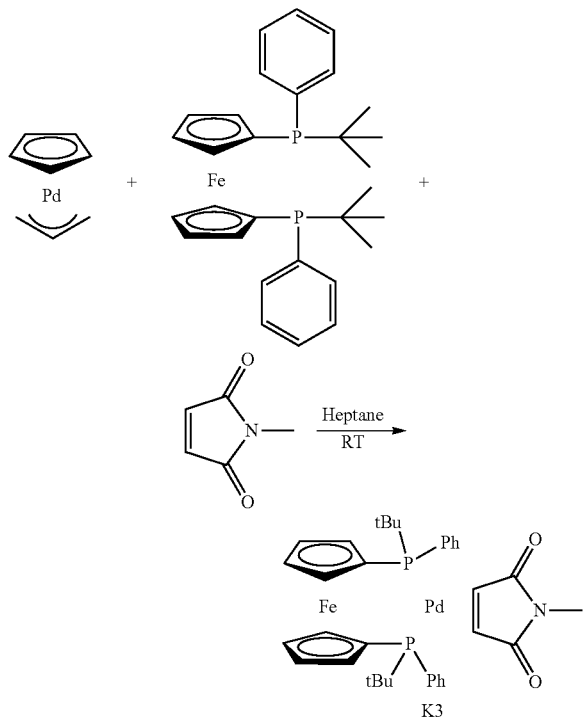

It is important in this reaction is that the maleimide sublimes beforehand (at 100° C. and $1\cdot10^{-3}$ mbar). Sublimed N-methylmaleimide is a white crystalline solid. Analogously to the synthesis with naphthoquinone (see experiment 50), 287 mg (80%) of product is obtained as a yellow solid which can be crystallized easily as follows:

42 mg of complex K3 are dissolved in 1-2 ml of toluene. 6 ml of heptane are added to the clear yellow solution. The solution does not turn cloudy. The volume is reduced by one third, and a yellow solid precipitates out. A bit more toluene is added thereto and the mixture is heated on a water bath at 60° C. The almost clear solution is filtered through Celite and the clear yellow filtrate is placed in the refrigerator at 3° C. After 4 days, yellow/brown crystals suitable for x-ray crystallography have formed.

$^1$H NMR (400 MHz, $C_6D_6$) δ 8.07 (m, 1H, CH arom), 7.98 (m, 1H, CH arom), 7.64-7.53 (m, 2H, CH arom), 7.23-7.12 (m, 3H, CH arom), 6.98 (m, 3H, CH arom), 4.49-4.36 (m, 2H, Cp or vinyl), 4.36-4.28 (m, 1H, Cp or vinyl), 4.10 (m, 0.5H, Cp or vinyl), 4.08-4.00 (m, 2H, Cp or vinyl), 3.88-3.81 (m, 2H, Cp or vinyl), 3.75 (m, 1,5H, Cp or vinyl), 3.59 (m, 1H, Cp or vinyl), 3.13 (s, 1H, $CH_3$), 3.05 (s, 1.5H, $CH_3$), 2.99 (s, 0.5H, $CH_3$), 1.33-1.16 (m, 18H, tBu).

$^{31}$P NMR (161 MHz, $C_6D_6$) δ=48.83 (d, Hz, J=17.4 Hz), 47.8 (d, Hz, J=17.4 Hz), 47.23 (s), 46.54 (s).

HRMS (ESI) m/z$^+$ calculated for $C_{35}H_{41}FeNO_2P_2Pd$ (M+Na)$^+$ 754.09044.

This is an isomer mixture which, in the $^{31}$P NMR, shows 6 different phosphorus signals and suggests 3 diastereomeric complexes.

The crystal structure consists of two diastereomeric complexes.

High-Pressure Experiments

Feedstocks:

Methanol (MeOH)

Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which are removed by distillation after the reaction.

A process practised in industry for oligomerization of C4 olefins is called the "OCTOL process". Within the patent literature, DE102008007081A1, for example, describes an oligomerization based on the OCTOL process. EP1029839A1 is concerned with the fractionation of the C8 olefins formed in the OCTOL process.

Technical di-n-butene consists generally to an extent of 5% to 30% of n-octenes, 45% to 75% of 3-methylheptenes, and to an extent of 10% to 35% of 3,4-dimethylhexenes. Preferred streams contain 10% to 20% n-octenes, 55% to 65% 3-methylheptenes, and 15% to 25% 3,4-dimethylhexenes.

PTSA hereinafter always refers to para-toluenesulphonic acid monohydrate.

General Experiment Description for Reactions in Batchwise Mode:

The appropriate amounts of substrate, palladium salt, acid and alcohol are mixed under argon in a 50 ml Schlenk vessel while stirring with a magnetic stirrer.

A 100 ml steel autoclave from Parr provided with a gas inlet and a gas outlet valve, a digital pressure transducer, a temperature sensor and a ball valve, and an installed capillary for sampling, is freed of oxygen by means of vacuum and argon purging three times. Subsequently, the reaction solution from the Schlenk vessel is introduced by means of a capillary into the autoclave in an argon counterflow through the ball valve. Subsequently, either the appropriate amount of CO is injected at room temperature and then the autoclave is heated up to reaction temperature (reactions that are not run under constant pressure) or the autoclave is first heated up to reaction temperature and then the CO is injected by means of a burette connected to the autoclave by means of a pressure reducer. This burette is then filled with CO to about 100 bar and, during the reaction, supplies the CO required at a constant pressure. This burette has a dead volume of about 30 ml and is provided with a digital pressure transducer. Then the reaction is conducted at the required temperature for the appropriate time while stirring. In the course of this, by means of software (Specview from SpecView Corporation) and a Parr 4870 process controller and a 4875 power controller, data for the pressure variation in the autoclave and in the gas burette are recorded. These data are used to generate Excel tables, which are used at a later stage to create diagrams which show gas consumptions and hence conversions over time. If required, via the capillary, the GC samples are collected and analysed. For this purpose, a suitable exact amount (2-10 ml) of isooctane as internal standard is also added to the Schlenk vessel before the reaction. These also give information about the course of the reaction. At the end of the reaction, the autoclave is cooled down to room temperature, the pressure is cautiously released, isooctane is added if necessary as internal standard, and a GC analysis or, in the case of new products, a GC-MS analysis is conducted.

General Experimental Method for Autoclave Experiments in Glass Vials:

A 300 ml Parr reactor is used. Matched to this is an aluminium block of corresponding dimensions which has been manufactured in-house and which is suitable for heating by means of a conventional magnetic stirrer, for example from Heidolph. For the inside of the autoclave, a round metal plate of thickness about 1.5 cm was manufactured, containing 6 holes corresponding to the external diameter of the glass vials. Matching these glass vials, they are equipped with small magnetic stirrers. These glass vials are provided with screw caps and suitable septa and charged, using a special apparatus manufactured by glass blowers, under argon with the appropriate reactants, solvents and catalysts and additives. For this purpose, 6 vessels are filled at the same time; this enables the performance of 6 reactions at the same temperature and the same pressure in one experiment. Then these glass vessels are closed with screw caps and septa, and a small syringe cannula of suitable size is used to puncture each of the septa. This enables gas exchange later in the reaction. These vials are then placed in the metal plate and the latter is transferred into the autoclave under argon. The autoclave is purged with CO and filled at room temperature with the CO pressure intended. Then, by means of the magnetic stirrer, under magnetic stirring, the autoclave is heated to reaction temperature and the reaction is conducted for the appropriate period. Subsequently, the autoclave is cooled down to room temperature and the pressure is slowly released. Subsequently, the autoclave is purged with nitrogen. The vials are taken from the autoclave, and a defined amount of a suitable standard is added. A GC analysis is effected, the results of which were used to determine yields and selectivities.

The experiment can also be conducted in a corresponding manner in a 600 ml Parr reactor, using a metal plate with 12 holes loaded with 12 reaction vessels.

Analysis:

GC analysis of 2-octene: For the GC analysis, an Agilent 7890A gas chromatograph having a 30 m HP5 column is used. Temperature profile: 35° C., 10 min; 10° C./min to 200° C.; the injection volume is 1 µl with a split of 50:1.

Retention times for 2-octene and products: 10.784-13.502 min

The esters formed from 2-octene are referred to hereinafter as MINO (methyl isononanoate).

Retention time for ether products of unknown isomer distribution: 15.312, 17.042, 17.244, 17.417 min Retention time for iso-C9 esters 19.502-20.439 min (main peak: 19.990 min)

Retention time for n-C9 esters: 20.669, 20.730, 20.884, 21.266 min.

The n/iso ratio indicates the ratio of olefins converted terminally to esters to olefins converted internally to esters.

The n selectivities reported hereinafter relate to the proportion of terminal methoxycarbonylation based on the overall yield of methoxycarbonylation products.

Unless stated otherwise, relative molar amounts in mol % hereinafter relate to the molar amount of olefin (substrate).

Methoxycarbonylation of 2-Octene with Different Ligands

A 25 ml Schlenk vessel was charged with a stock solution composed of Pd(acac)$_2$ (1.95 mg, 6.4 µmol), MeSO$_3$H (6.4 µl, 98.55 µmol) and MeOH (10 ml, 24.69 mmol). A 4 ml vial was charged with 0.16 mol % of the ligand specified (based on the molar amount of 2-octene) and a magnetic stirrer bar was added. Thereafter, 1.25 ml of the clear yellow stock solution and 2-octene (315 µl, 2 mmol) were injected with a syringe. The molar proportions based on the molar amount of 2-octene are then 0.04 mol % for Pd(acac)$_2$ and 0.6 mol % for MeSO$_3$H. The vial was placed into a sample holder which was in turn inserted into a 300 ml autoclave from Parr Instruments under an argon atmosphere. After the autoclave had been purged three times with nitrogen, the CO pressure was adjusted to 40 bar. The reaction proceeded at 120° C. for 5 hours. On conclusion of the reaction, the autoclave was cooled down to room temperature and cautiously decompressed. Isooctane was added as internal GC standard. Yield of methyl nonanoate and regioselectivity were determined by means of GC. The results are compiled in the following table:

| Example | Ligand | Yield | n/iso ratio |
|---|---|---|---|
| 1* | 1,1'-bis(tert-butylphenylphosphino)ferrocene | 85% | 83/17 |
| 2 (CE) | 1-(diphenylphosphino)-1'-(diadamantylphosphino)ferrocene | 53% | 75/25 |
| 3 (CE) | 1-(diphenylphosphino)-1'-(dicyclohexylphosphino)ferrocene | 36% | 75/25 |
| 4 (CE) | 1,1'-bis(isopropylphenylphosphino)ferrocene | 55% | 77/23 |
| 5 (CE) | 1-(diphenylphosphino)-1'-(diisopropylphosphino)ferrocene | 47% | 73/27 |
| 6 (CE) | 1-(diphenylphosphino)-1'-(tert-butylphenylphosphino)ferrocene | 65% | 70/30 |
| 7 (CE) | 1,1'-bis(di(1,4-di(trifluoromethyl)phenyl)phosphino)ferrocene | 0% | — |

CE: comparative example
*inventive example

This experiment shows that, with the 1,1'-bis(tert-butylphenylphosphino)ferrocene ligand according to the invention, a distinctly higher yield and greater n/iso specificity can be achieved than with structurally similar ferrocenyl ligands known from the prior art.

Methoxycarbonylation of di-n-butene with Different Ligands

A 50 ml Schlenk vessel was charged with a stock solution composed of [Pd(acac)$_2$] (3.9 mg, 12.9 µmol), MeSO$_3$H (methanesulphonic acid) (13 µl, 197.1 µmol) and MeOH (20 ml). A 4 ml vial was charged with 0.16 mol % of the ligand specified (based on the molar amount of di-n-butene) and a magnetic stirrer bar was added. Thereafter, 1.25 ml of the clear yellow stock solution and di-n-butene (315 µl, 2 mmol) were injected with a syringe. The molar proportions based on the molar amount of 2-octene are then 0.04 mol % for Pd(acac)$_2$ and 0.6 mol % for MeSO$_3$H. The vial was placed into a sample holder which was in turn inserted into a 600 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane was added as internal GC standard. Yield of methyl isononanoate (MINO) and regioselectivity were determined by means of GC. The results are compiled in the following table:

| Example | Ligand | Yield | n/iso ratio |
|---|---|---|---|
| 1% | 1,1'-bis(tert-butylphenylphosphino)ferrocene | 73% | 86/14 |

-continued

| Example | Ligand | Yield | n/iso ratio |
|---|---|---|---|
| 2 (CE) | 1,2-bis(di-tert-butylphosphinomethyl)benzene | 49% | 94/6 |
| 3 (CE) | 1-(di-tert-butylphosphino)-1'-(diphenylphosphino)ferrocene | 18% | 79/21 |
| 4 (CE) | 1-(diphenylphosphino)-1'-(diisopropylphosphino)ferrocene | 12% | 78/22 |
| 5 (CE) | 1-(diphenylphosphino)-1'-(tert-butylphenylphosphino)ferrocene | 16% | 77/23 |
| 6 (CE) | 1,1'-bis(isopropylphenylphosphino)ferrocene | 22% | 80/20 |

CE: comparative example
* inventive example

In this experiment too, with the ligand according to the invention, a distinctly better yield coupled with higher n/iso selectivity is achieved than with structurally similar ferrocenyl ligands or the known DTBPMB ligand.

Methoxycarbonylation of di-n-butene with Preformed Complexes

A 100 ml steel autoclave is charged under argon with 0.04 mol % of the complex specified and 1,1'-bis(tert-butylphenylphosphino)ferrocene (29.6 mg, 0.12 mol %). Subsequently, MeOH (30 ml) and di-n-butene (7.54 ml, 48 mmol) and PTSA (54.7 mg, 0.6 mol %) are added. The autoclave is charged at room temperature with CO of purity 4.7 to 40 bar and the reaction is conducted at 120° C. for 20 hours. Subsequently, the autoclave is cooled down and the pressure is slowly released. The contents of the autoclave are transferred to a Schlenk vessel. 5 ml of isooctane are added as internal standard, and the yield of methyl isononanoate (MINO) and regioselectivity are determined by means of GC analysis. The results are compiled in the following table:

| Complex | Structure | Yield | n/iso selectivity |
|---|---|---|---|
| K1* | 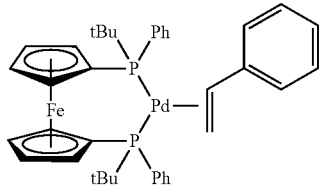 | 76% | 87/13 |
| K2* | 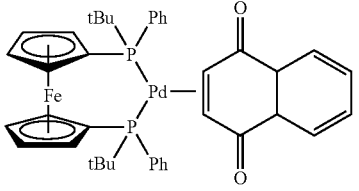 | 72% | 87/13 |
| K3* | 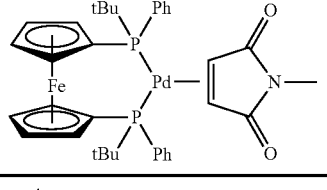 | 72% | 87/13 |

*inventive examples

This experiment shows that it is just as possible to obtain good results with the preformed complexes as it is with the complexes formed in situ.

The invention claimed is:

1. Process comprising the following process steps:
   a) initially charging an ethylenically unsaturated compound;
   b) adding a compound of formula (1)

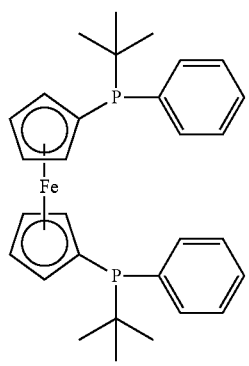

(1)

and a compound comprising Pd,
   or adding a complex comprising Pd and the compound of formula (1);
   c) adding an alcohol;
   d) feeding in CO;
   e) heating the reaction mixture, with conversion of the ethylenically unsaturated compound to an ester.

2. The process of claim 1, wherein the complex is selected from one of the following K1 to K3:

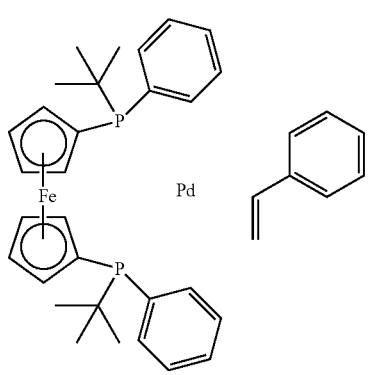

(K1)

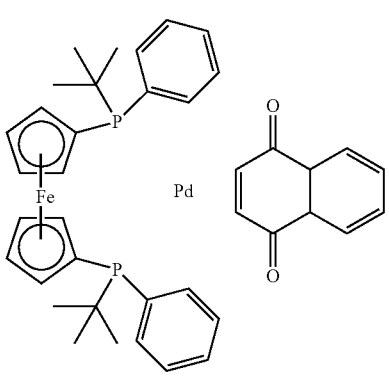

(K2)

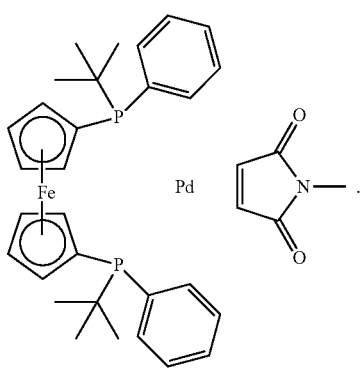

(K3)

3. Process according to claim 1,
wherein the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

4. Process according to claim 1,
wherein the ethylenically unsaturated compound comprises 8 to 22 carbon atoms.

5. Process according to claim 1,
wherein the compound comprising Pd in process step b) is selected from palladium dichloride, palladium(II) acetylacetonate, palladium(II) acetate, dichloro(1,5-cyclooctadiene)palladium(II), bis(dibenzylideneacetone)palladium, bis(acetonitrile)dichloropailadium(II), palladium(cinnamyl) dichloride.

6. Process according to claim 1,
wherein the alcohol in process step c) is selected from methanol, ethanol, 1-propanol, 1-butanol, 1-pentanol, 1-hexanol, 2-propanol, tert-butanol, 3-pentanol, cyclohexanol, phenol, or mixtures thereof.

7. A process for catalysis of an alkoxycarbonylation reaction, comprising: introducing a compound of formula (1)

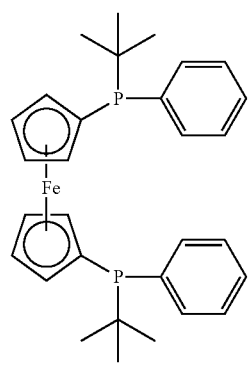

(1)

or a complex comprising Pd and the compound of formula (1).

* * * * *